US008328778B2

(12) United States Patent
Michaels et al.

(10) Patent No.: US 8,328,778 B2
(45) Date of Patent: *Dec. 11, 2012

(54) LIQUID COLLECTION SYSTEM AND RELATED METHODS

(75) Inventors: Thomas L. Michaels, McCullom Lake, IL (US); Russ A. Johnson, Spring Grove, IL (US); Jeannie Thomas, Riverwoods, IL (US)

(73) Assignee: Allegiance Corporation, McGaw Park, IL (US)

( * ) Notice: Subject to any disclaimer, the term of this patent is extended or adjusted under 35 U.S.C. 154(b) by 107 days.

This patent is subject to a terminal disclaimer.

(21) Appl. No.: 12/728,034

(22) Filed: Mar. 19, 2010

(65) Prior Publication Data

US 2010/0185166 A1    Jul. 22, 2010

Related U.S. Application Data

(63) Continuation of application No. 11/700,355, filed on Jan. 31, 2007.

(51) Int. Cl.
*A61M 1/00* (2006.01)

(52) U.S. Cl. ......... 604/317; 604/318; 604/322; 604/326

(58) Field of Classification Search .................. 604/317, 604/318, 322, 326
See application file for complete search history.

(56) References Cited

U.S. PATENT DOCUMENTS

| | | | |
|---|---|---|---|
| 3,680,560 A | 8/1972 | Pannier, Jr. et al. | |
| 3,782,414 A | 1/1974 | Holbrook | |
| 3,838,691 A | 10/1974 | Paludan et al. | |
| 3,843,016 A | 10/1974 | Bornhorst et al. | |
| 3,855,997 A | 12/1974 | Sauer | |
| 3,906,935 A | 9/1975 | Raia et al. | |
| 4,014,329 A | 3/1977 | Welch et al. | |
| 4,460,361 A | 7/1984 | Nichols | |
| 4,475,904 A | 10/1984 | Wang | |
| 4,475,984 A | 10/1984 | Cael | |
| 4,681,571 A | 7/1987 | Nehring | |
| 4,769,019 A | 9/1988 | Kerwin | |
| 5,124,126 A | 6/1992 | Ripp | |
| 5,195,961 A | 3/1993 | Takahashi et al. | |
| 5,242,434 A | 9/1993 | Terry | |
| 5,370,610 A | 12/1994 | Reynolds | |
| 2005/0215961 A1 | 9/2005 | Romano et al. | |
| 2007/0135779 A1 | 6/2007 | Lalomia et al. | |

FOREIGN PATENT DOCUMENTS

EP    1 031 357 A2    8/2000

(Continued)

OTHER PUBLICATIONS

Non-Final Office Action in related U.S. Appl. No. 12/728,062 dated Oct. 19, 2011.

(Continued)

*Primary Examiner* — Jacqueline F. Stephens
(74) *Attorney, Agent, or Firm* — Arent Fox LLP

(57) ABSTRACT

Various embodiments of a fluid collection system having multiple storage chambers are disclosed. In an exemplary embodiment, the system may include a first chamber in fluid communication with a suction source and a second chamber in fluid communication with the first chamber. The second chamber may have a volume less than a volume of the first chamber. The second chamber may also comprise an inlet port for connecting to an external tube. The system may be configured to selectively drain liquid from the second chamber into the first chamber.

12 Claims, 10 Drawing Sheets

FOREIGN PATENT DOCUMENTS

| | | |
|---|---|---|
| WO | WO 88/10124 A1 | 12/1988 |
| WO | WO 01/83003 A1 | 11/2001 |
| WO | WO 2006/041406 A1 | 4/2006 |

OTHER PUBLICATIONS

Non-Final Office Action in related U.S. Appl. No. 12/728,048 dated Jan. 26, 2012.

Final Office Action in related U.S. Appl. No. 12/728,062 dated Mar. 2, 2012.

Final Office Action in related U.S. Appl. No. 12/728,057 dated Mar. 8, 2012.

Non-Final Office Action in related U.S. Appl. No. 12/728,057 dated Oct. 17, 2011.

LIQUID COLLECTION SYSTEM AND RELATED METHODS

CROSS-REFERENCE TO RELATED APPLICATION

This application is a continuation of application Ser. No. 11/700,355, filed Jan. 31, 2007, the entire specification claims and drawings of which are incorporated herewith by reference.

FIELD OF THE INVENTION

Embodiments of the present invention relate generally to fluid collection systems and related methods. More specifically, particular embodiments of the invention relate to a liquid collection system having multiple storage chambers and related methods of use.

DESCRIPTION OF RELATED ART

Hospital operating rooms and other healthcare facilities generate a large volume of liquid waste, which may include irrigation liquids and secretions removed from patient's body (e.g., blood and other bodily liquids). One study shows that a typical operating room generates about two tons of liquid waste each month. Such liquid waste is considered infectious medical waste and must be disposed of in accordance with stringent safety standards established by federal and state regulations.

To collect and dispose such liquid waste, suction canisters are typically used in hospital operating rooms and other healthcare facilities. A suction canister is a temporary storage container that uses suction to create a negative pressure inside the canister to drain liquids or secretions from the patients' body. After each medical procedure (e.g., surgery), the canister containing the liquid waste is transported to a utility area to be disposed of as red-bag waste or to be emptied, cleaned, and disinfected for reuse. A new or cleaned canister is then brought into the operating room for a next medical procedure. This process can be labor intensive and time consuming. Furthermore, since this process is performed every time following each medical procedure, it may increase the clinicians' risk of exposure to potentially hazardous waste.

In an effort to reduce the number of such frequent disposal processes, a waste system equipped with a large reusable container (e.g., 20 liters) and a disposable manifold has been suggested to enable continued waste collection during multiple medical procedures. Such a system, however, cannot provide adequate information about the content and amount of liquid being collected during a medical procedure, since the liquid being collected directly flows into the large container and is mixed with the previously collected waste. Thus, physicians and clinicians participating in the procedure may not be able to make a quick and simple visual assessment of the contents and amount of liquid being collected to determine, for example, the amount of blood loss or the composition of the liquid, which may be critical in certain types of medical procedures.

Accordingly, there is a need for an improved waste management system that may overcome one or more of the problems discussed above. In particular, there is a need for an improved liquid collection system that may reduce the number of disposal processes and, at the same time, provides adequate information (e.g., volume and contents) about the liquid being collected.

SUMMARY OF THE INVENTION

Therefore, various exemplary embodiments of the invention may provide a liquid collection system that utilizes multiple storage chambers to improve labor efficiency, safety, and convenience of the medical personnel participating in a liquid collection process. For example, the multiple storage chambers may provide a clean collection interface that may reduce the need for frequent disposal processes, thereby reducing the medical personnel's risk of exposure to potentially hazardous waste.

While the present invention will be described in connection with a particular medical waste collection process, various embodiments of the invention may be used in other suitable medical and non-medical applications, such as, for example, a medical or non-medical cleaning process.

To attain the advantages and in accordance with the purpose of the invention, as embodied and broadly described herein, one exemplary aspect of the invention may provide a fluid collection system comprising a first chamber in fluid communication with a suction source and a second chamber in fluid communication with the first chamber. The second chamber may have a volume less than a volume of the first chamber. The second chamber may also comprise an inlet port for connecting to an external tube. The system may be configured to selectively drain liquid from the second chamber into the first chamber.

In another exemplary aspect, the second chamber may be removably connected to the first chamber. In still another exemplary aspect, the second chamber may comprise an overflow mechanism configured to allow liquid collected in the second chamber to flow into the first chamber when a liquid level in the second chamber rises above a predetermined level.

According to still yet another exemplary aspect, the fluid communication between the first chamber and the second chamber may comprise a conduit having a first end extending to an upper portion of the second chamber and a second end communicating with the first chamber. The second end of the conduit may extend into an interior of the first chamber. In some exemplary embodiments, the conduit may extend vertically across a bottom wall of the second chamber.

In some exemplary aspects, the system may comprise a drain passage communicating between the first chamber and the second chamber. The drain passage may comprise a valve configured to open and close the drain passage so as to selectively allow the liquid collected in the second chamber to flow from the second chamber to the first chamber. In various exemplary embodiments, the drain passage may comprise an opening in the second chamber. For example, the valve may comprise a plate member having an opening, and the second chamber and the plate member may be movable relative to one another between an open position, in which the opening of the second chamber is in alignment with the opening of the plate member, and a closed position, in which the opening of the second chamber is not in alignment with the opening of the plate member.

In another aspect of the invention, the system may comprise a support member having a first end configured to communicate with the second chamber and a second end configured to be removably placed on a top of the first chamber in fluid communication with an interior of the first chamber. The support member may be configured to establish the fluid communication between the first chamber and the second chamber when the support member is placed on the top of the first chamber.

According to various exemplary aspects, the second chamber may comprise a main body, a lid having the inlet port and configured to substantially close the main body, and a liner disposed inside the main body. The lid and the liner may define an interior space in fluid communication with the inlet port, and the main body and the liner may define an exterior space.

In another exemplary aspect, the fluid connection between the first chamber and the second chamber may comprise a first line for communicating between the first chamber and the interior space, a second line for communicating between the first chamber and the exterior space, and a valve configured to open and close the second line. In some exemplary embodiments, the first line may comprise a first passage and a second passage, where ends of the first and second passages inside the second chamber may be located at different elevations from one another. The first line may define both the first passage and the second passage in a single conduit. In one exemplary embodiment, the second line may be branched off from the first line.

According to still another exemplary aspect, the fluid communication between the first chamber and the second chamber may be configured such that, with the inlet port closed, closing the valve may cause the interior space to collapse and to thereby cause the fluid collected in the second chamber to flow into the first chamber.

In one exemplary aspect, the liner may be configured to prevent direct contact between the fluid collected in the interior space and the main body. In another exemplary aspect, at least a portion of the second chamber may comprise a transparent material. In still another exemplary aspect, the second chamber may comprise volume graduations.

Another exemplary aspect of the invention may provide a method of collecting liquid. The method may comprise providing a first chamber in fluid communication with a suction source, connecting a second chamber in fluid communication with the first chamber, the second chamber having a volume smaller than a volume of the first chamber, and the second chamber being connected to an external tube, collecting liquid in the second chamber via the external tube, and selectively draining the liquid collected in the second chamber into the first chamber. In still another exemplary aspect, the method may comprise removing the second chamber from the first chamber.

In an exemplary aspect, selectively draining the liquid may comprise allowing the liquid to flow into the first chamber when a liquid level in the second chamber rises above a predetermined level. In another exemplary aspect, connecting the second chamber in fluid communication with the first chamber may comprise providing a conduit having a first end extending to an upper portion of the second chamber and a second end communicating with the first chamber. The conduit may extend vertically across a bottom wall of the second chamber.

In still another exemplary aspect, selectively draining the liquid may comprise providing a valve configured to open and close a flow passage communicating between the first chamber and the second chamber, so as to selectively allow the liquid collected in the second chamber to flow into the first chamber.

In still yet anther exemplary aspect, the flow passage may comprise a first opening in the second chamber and a plate member having a second opening. The second chamber and the plate member may be rotatable relative to one another between an open position, in which the first opening is aligned with the second opening, and a closed position, in which the first opening is not aligned with the second opening.

In one exemplary aspect, connecting the second chamber in fluid communication with the first chamber may comprise providing a support member having a first end configured to communicate with the second chamber and a second end configured to be removably placed on a top of the first chamber in fluid communication with an interior of the first chamber. The support member may establish the fluid communication between the first chamber and the second chamber when the support member is placed on the top of the first chamber.

In another exemplary aspect, the method may comprise providing a liner between a main body and a lid of the second chamber, such that the lid and the liner define an interior space in fluid communication with the external tube and such that the main body and the liner define an exterior space. Selectively draining the liquid may comprise collapsing the liner using the suction source to drain the liquid collected in the second chamber into the first chamber.

According to some exemplary aspects, connecting the second chamber in fluid communication with the first chamber may comprise connecting a first line between the first chamber and the interior space, and connecting a second line between the first chamber and the exterior space. In an exemplary embodiment, the first line may comprise a first passage and a second passage, and ends of the first and second passages inside the second chamber may be located at different elevations from one another. In another exemplary embodiment, the second line may be branched off from the first line. Selectively draining the liquid may comprise closing the second line so as to cause the internal space to collapse and to cause the liquid collected in the second chamber to flow into the first chamber.

In various exemplary aspect, collecting the liquid may comprise collecting liquid during a medical procedure. In another exemplary aspect, the method may further comprise applying suction to the second chamber from the first chamber.

Some exemplary aspects of the invention may also provide a liquid collection chamber comprising a main body configured to collect liquid, an inlet port for connecting to an external tube, and a flow passage communicating between an interior and an exterior of the main body. The chamber may be configured to selectively drain liquid collected in the main body through the flow passage without tilting the main body.

In another exemplary aspect, the chamber may comprise a lid configured to substantially close an opening of the main body, and the lid may comprise the inlet port. In still another exemplary aspect, the chamber may further comprise a liner disposed inside the main body. The lid and the liner may define a first space in fluid communication with the inlet port, and the main body and the liner may define a second space.

According to various exemplary embodiments, the flow passage may comprises a first line for communicating between a suction source and the first space, a second line for communicating between the suction source and the second space, and a valve configured to open and close the second line. The first line may comprise a first passage and a second passage, and ends of the first and second passages inside the main body may be located at different elevations from one another. In some exemplary embodiments, the first line may define both the first passage and the second passage in a single conduit.

In another exemplary aspect, the second line may be branched off from the first line. In still another exemplary aspect, the flow passage may be configured such that, with the inlet port closed, closing the valve may cause the first space to collapse and to thereby cause the liquid collected in the main body to flow out of the main body. In one exemplary aspect, the liner may be configured to prevent direct contact between the liquid collected in the first space and the main body.

According to one exemplary aspect, the flow passage may be positioned at an upper portion of the main body. In another exemplary aspect, the chamber may comprise an overflow mechanism configured to allow liquid collected in the main body to drain out of the main body when a liquid level in the main body rises above a predetermined level.

In still another exemplary aspect, the chamber may comprise a suction port for connecting to a suction source. In still yet another exemplary aspect, the flow passage may comprise the suction port. In various exemplary embodiments, the suction port may comprise a conduit having a first end extending to an upper portion of the main body and a second end communicating with the exterior of the main body. In an exemplary embodiment, the conduit may extend vertically across a bottom wall of the main body.

In another exemplary aspect, the flow passage may comprise a valve configured to open and close the flow passage so as to selectively drain liquid collected in the main body to the exterior. The flow passage may comprise a first opening in the main body, and the valve may comprise a plate member having a second opening. The main body and the plate member may be movable relative to one another between an open position, in which the first opening is in alignment with the second opening, and a closed position, in which the first opening is not in alignment with the second opening.

According to another exemplary aspect, the chamber may comprise a support member having a first end configured to communicate with the main body and a second end configured to be removably placed on a storage container in fluid communication with an interior of the storage container. The support member may be configured to establish a fluid communication between the interior of the main body and the interior of the storage container when the support member is placed on the storage container.

Still another exemplary aspect may provide a method of performing a medical procedure. The method may comprise placing a second chamber in fluid communication with a first chamber, the first chamber having a volume greater than a volume of the second chamber, collecting liquid in the second chamber during a medical procedure, transferring the liquid collected in the second chamber into the first chamber, replacing at least a portion of the second chamber with a clean unit, and placing the removed portion in a waste container.

In some exemplary embodiment, replacing at least a portion of the second chamber may comprise removing the second chamber from the first chamber and replacing the second chamber with a third chamber configured like the second chamber.

According to another exemplary aspect, the method may comprise providing the second chamber in fluid communication with a suction source. In still another aspect, collecting liquid may comprise drawing liquid into the second chamber via a suction tube connected to the second chamber.

In one exemplary aspect, transferring may comprise actuating a valve to open a flow passage connecting between the first chamber and the second chamber. In another exemplary aspect, placing the first chamber in fluid communication with the second chamber may comprise removably placing the second chamber on a top of the first chamber in fluid communication with an interior of the first chamber.

In various exemplary aspects, the method may comprise providing a liner between a main body and a lid of the second chamber, such that the lid and the liner define an interior space in fluid communication with an external tube and such that the main body and the liner define an exterior space. The method may also comprise collapsing the liner to transfer the liquid from the second chamber to the first chamber. In an exemplary aspect, replacing at least a portion of the second chamber may comprise removing the liner and the lid from the main body and placing another liner and another lid on the main body.

In another exemplary aspect, the method may comprise treating the liquid collected in the second chamber before transferring to the first chamber. In still another exemplary aspect, the method may comprise filtering the liquid collected in the second chamber before transferring to the first chamber. In still yet another exemplary aspect, the method may comprise applying suction to the second chamber via the first chamber.

According to various exemplary aspects, liquid collected in the second chamber may be from a first patient, and the method may comprise collecting liquid from a second patient in the clean unit. In an exemplary aspect, the first chamber may retain liquid collected from the first patient while liquid is being collected from the second patient in the clean unit.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

DESCRIPTION OF THE EMBODIMENTS

Reference will now be made in detail to exemplary embodiments consistent with the present invention, examples of which are illustrated in the accompanying drawings. Wherever possible, the same reference numbers will be used throughout the drawings to refer to the same or like parts.

Figure 1:
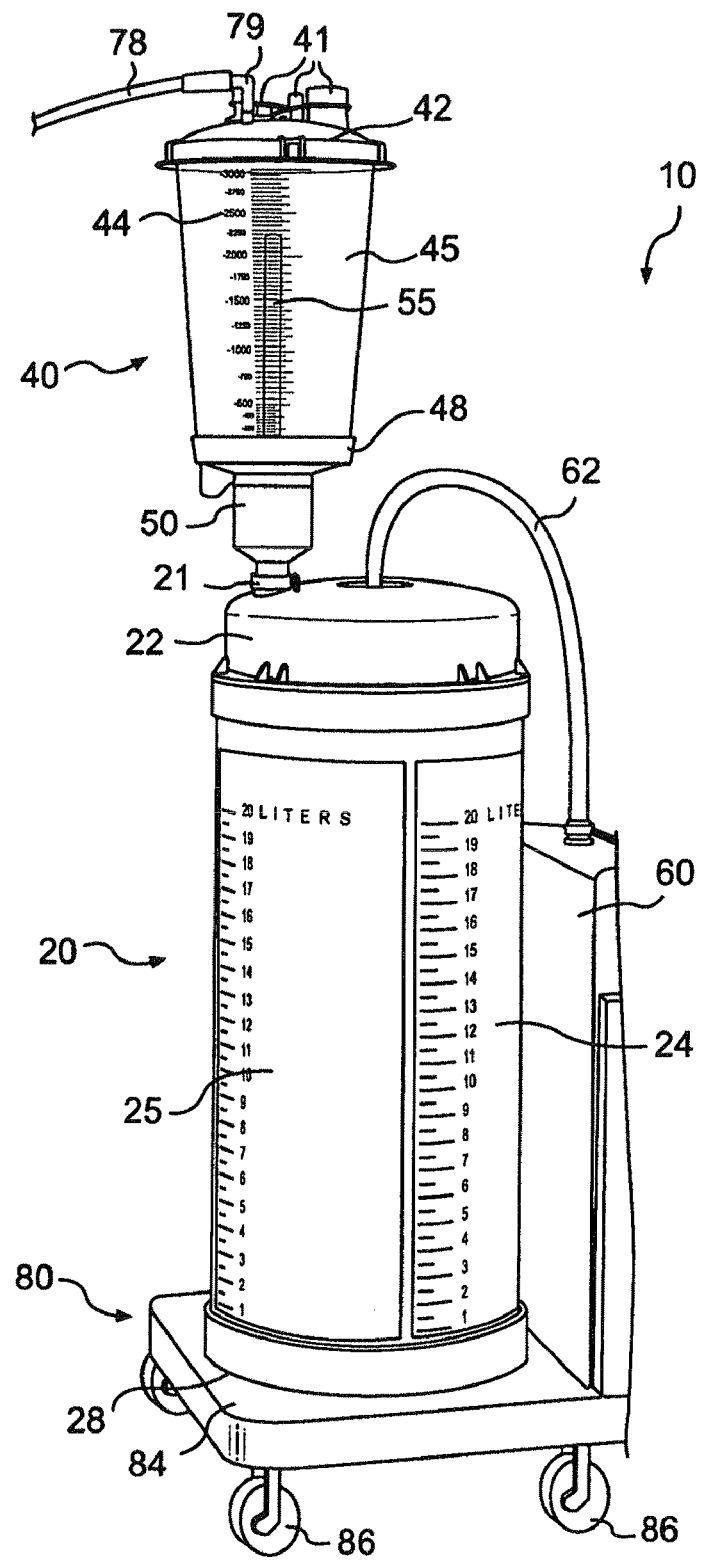
FIG. 1 is a perspective view of a liquid collection system, according to an exemplary embodiment of the invention.
Figure 2:
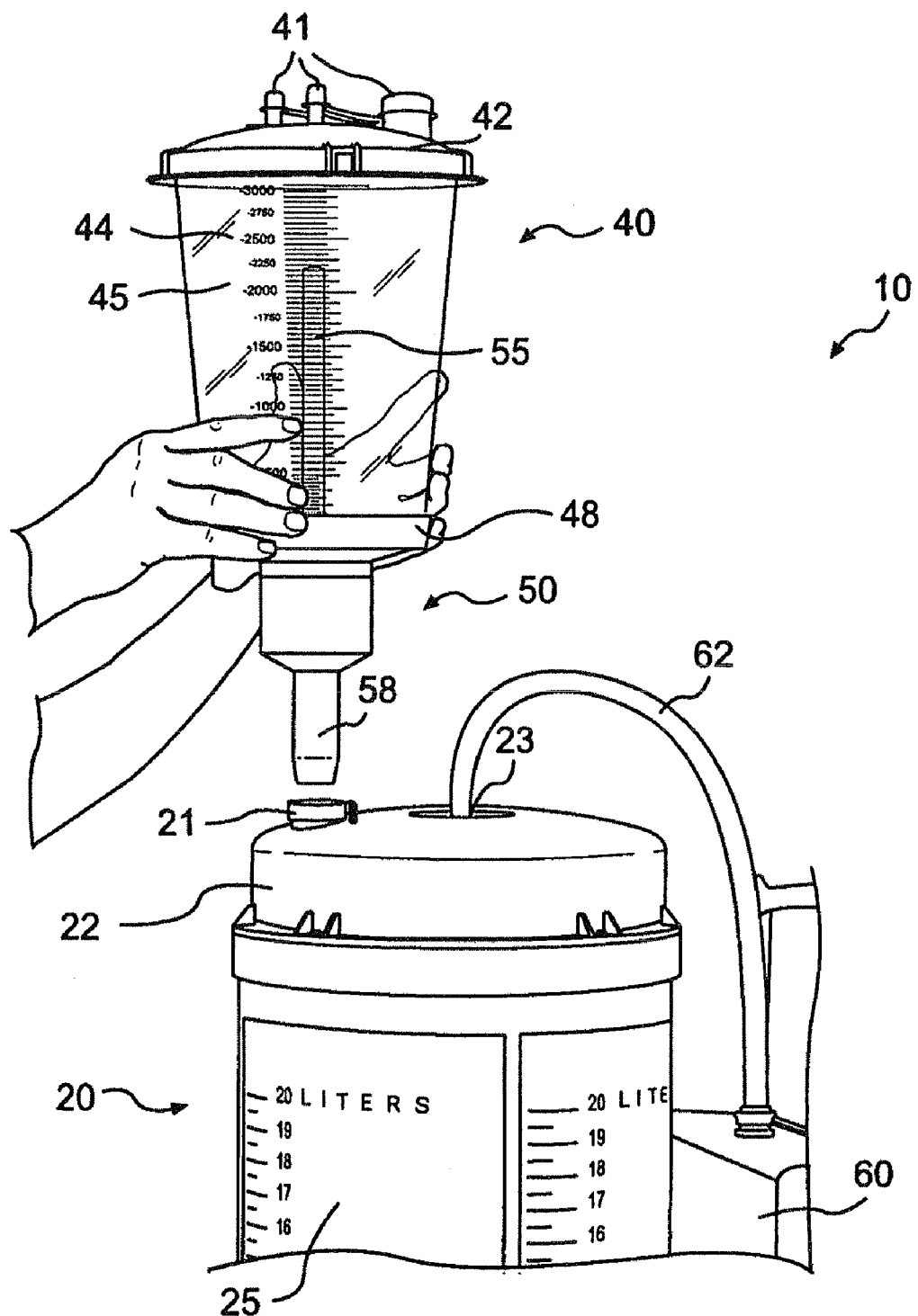
FIG. 2 is a partial perspective view of the liquid collection system of FIG. 1, illustrating that the second chamber may be removable from the first chamber.

FIGS. 1 and 2 show a multi-chamber liquid collection system 10, according to an exemplary embodiment of the invention. The system 10 may comprise a first chamber 20, a second chamber 40, and a suitable suction source 60. The suction source 60, which may be a portable unit, may comprise a suction pump or compressor to generate a negative pressure (e.g., vacuum) in the first and second chambers 20, 40. The negative pressure may be used to draw liquid into the collection system 10.

The term "liquid," as used herein, is not merely referring to a state of matter as defined in the thermodynamic and/or fluid mechanics art. Instead, the term "liquid" includes any solid particles that may incidentally flow with a liquid medium (e.g., irrigation fluid or blood) or that may be intentionally collected using a liquid medium. For example, when the fluid collection system 10 of the invention is used in a surgical procedure, the term "liquid" may refer to a combination of liquid medium (e.g., irrigation fluid, blood, and other bodily liquid from the patient) and any solid particles including, but not limited to, resected tissue removed from the patient's body.

As best shown in FIG. 1, the first chamber 20 may have a volume substantially greater than a volume of the second chamber 40. By way of examples only, in some exemplary embodiments, the volume of the first chamber may be about 20 liters, and the volume of the second chamber 40 may be about 3 liters. These volumes may vary depending upon the type of medical procedures and/or the anticipated amount of liquid to be collected. The first and second chambers 20, 40 may also have a variety of different shapes. For example, in various exemplary embodiments, the first chamber 20 may have a substantially cylindrical body 25 with a substantially flat bottom surface 28, and the second chamber 40 may have a generally tapering, frustoconical-shaped body 45, as best shown in FIG. 1. The first and second chambers 20, 40 may be made of a material that is sufficiently strong to withstand the negative pressure generated by the suction source 60.

As shown in FIG. 1, the first chamber 20 may include a cap 22 configured to close the top opening of the cylindrical body 25. The cap 22 may include at least two access ports: a first access port 23 for connecting to the suction source 60 via a suitable suction conduit 62 and a second access port 21 for communicating with the second chamber 40. The suction conduit 62 may be removable from the first chamber 20 and/or the suction source 60. As will be described later in detail, a portion of the second chamber 40 may be configured to engage the second access port 21 to establish liquid and suction connections between the first and second chambers 20, 40. Moreover, the connection between the first and second chambers 20, 40 may enable selective draining of liquid from the second chamber 40 to the first chamber 20.

At least a portion of the first chamber 20 may be transparent (or sufficiently translucent to visualize the liquid level inside the first chamber 20) so that the physicians and/or technicians participating in the medical procedure may determine the amount of liquid collected in the first chamber 20. The first chamber 20 may also include volume graduations 24 to more accurately measure the liquid amount. In some exemplary embodiments, the first chamber 20 may include a drain port (not shown) located at or near the bottom portion of the first chamber 20 for draining the liquid when desired.

Although not necessary, the system 10 may include a transporter unit 80 having a flat platform 84, on which the first chamber 20 may be placed, as shown in FIG. 1. The transporter unit 80 may also include a suitable holding member to secure the first chamber 20 to the transporter unit 80. The transporter unit 80 may also include wheels 86 to facilitate transport of the system 10. The suction source 60 may be integrally formed with, or separately provided to, the transporter unit 80.

The second chamber 40 may comprise a main body 45, a lid 42, and a base member 48, as best shown in FIG. 2. The second chamber 40 may be positioned at an elevation higher than an elevation of the first chamber 20, so that the liquid collected in the second chamber 40 can flow into the first chamber 20 via gravity. The second chamber 40 may be at least partially transparent to enable physicians and technicians to examine the amount and contents of the liquid being collected in the second chamber 40. The second chamber 40 may also include volume graduations 44 to more accurately measure the amount of liquid being collected.

The lid 42 may close the top opening of the main body 45 in a leak-tight manner. The lid 42 may include a connecting port 41 for connecting to a suction tube 78 (e.g., a suction tube used to collect patient fluids during a surgical procedure, a suction tube of a suction catheter, a G-tube, or a wound drain tube) via a suitable connector 79, as shown in FIG. 1. In some exemplary embodiments, including the embodiment shown in FIGS. 1 and 2, the lid 42 may include one or more additional ports 41. These ports 41 may be used to connect one or more additional medical devices simultaneously or to treat the liquid collected in the second chamber 40 with chemicals before being transferred to the first chamber 20. When not in use, these additional ports 41 may be closed with caps, which may be integrally attached to the lid 42. The connecting ports 41 may have various different sizes and shapes to accommodate various medical devices that may be used with the system 10.

Figure 3A:
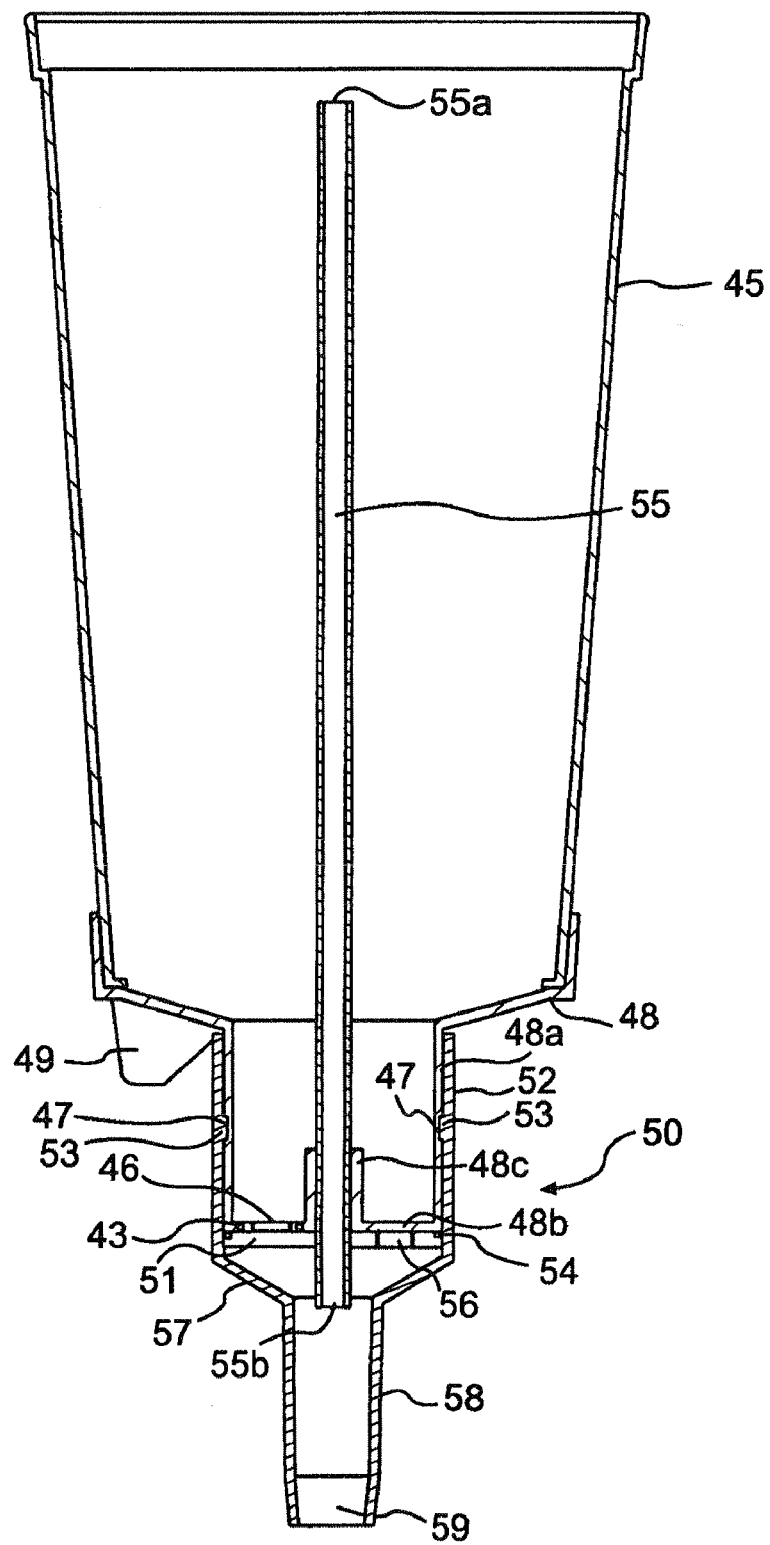
FIGS. 3A and 3B are cross-sectional views of the second chamber shown in FIGS. 1 and 2, illustrating liquid collection and liquid draining processes, respectively.
Figure 3B:
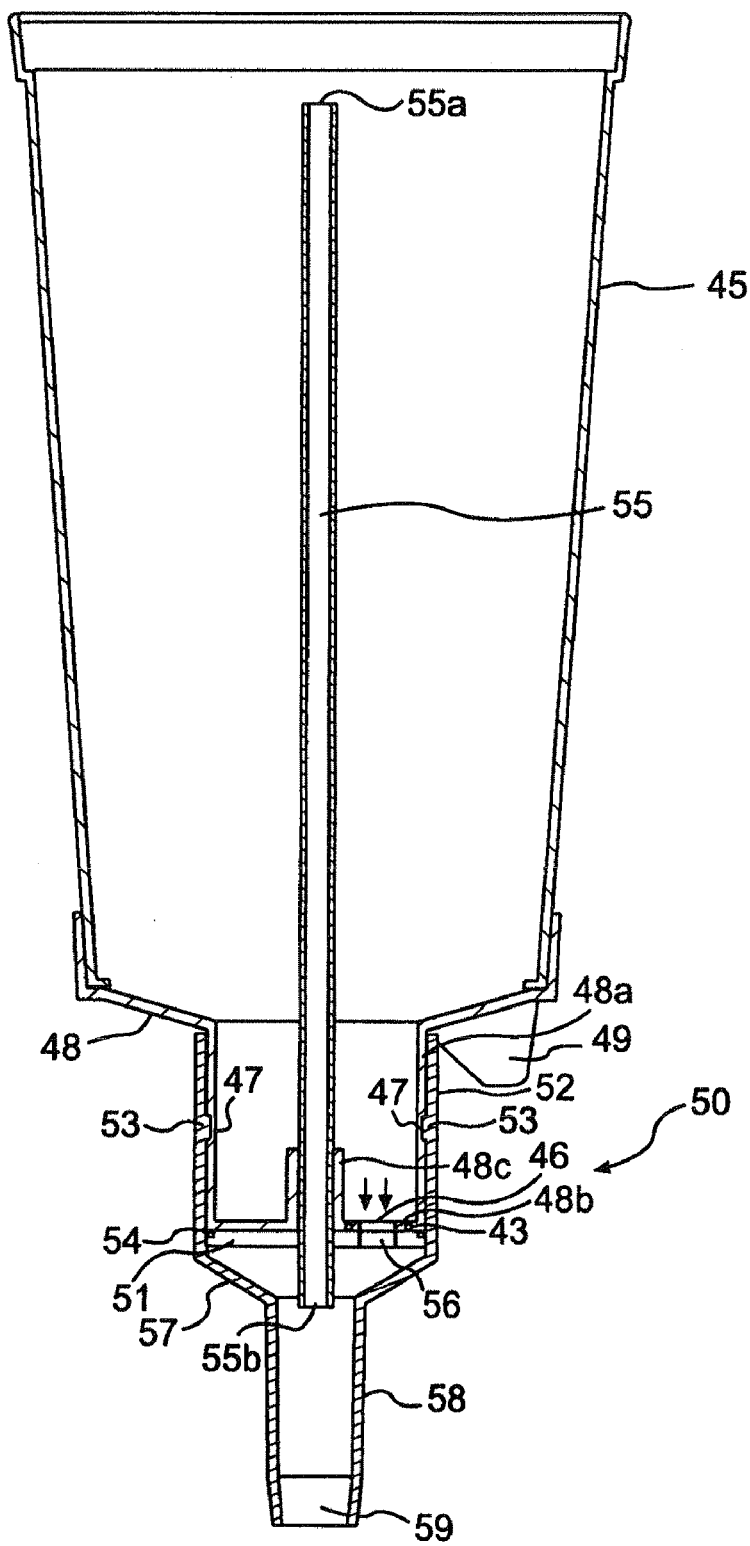

As best shown in FIGS. 3A and 3B, the base member 48 may have a funnel-like configuration having a wide portion for receiving a bottom portion of the main body 45 and a narrow portion defined by an outer wall 48a. In some exemplary embodiments, the base member 48 may be integrally formed with the main body 45. The base member 48 may include a transverse wall 48b extending across the outer wall 48a and an annular extension 48c extending substantially perpendicularly from the transverse wall 48b. The transverse wall 48b may define an opening 46, which, as will be described further herein, may be used to selectively drain the liquid collected in the second chamber 40 into the first chamber 20. In an exemplary embodiment, the transverse wall 48b may include more than one opening 46. The annular extension 48c may be configured to receive and hold a suction conduit 55. Any other suitable holding mechanism may be used alternatively or additionally to hold the suction conduit 55 inside the second chamber 40.

The suction conduit 55 has a first end 55a positioned near the top of the second chamber 40 and a second end 55b positioned below the base member 48. When the opening 46 of the transverse wall 48b is closed, the suction conduit 55 may provide the only passage that communicates between the first and second chambers 20, 40 and, as will be explained further herein, may serve as both a suction passage and an overflow passage between the first and second chambers 20, 40.

The elevational position of the first end 55a inside the second chamber 40 may correspond to the maximum liquid level desired in the second chamber 40. For example, referring to FIGS. 4 and 5, as the liquid level inside the second chamber 40 rises above the first end 55a of the suction conduit 55, the liquid above the first end 55a may enter the first end 55a of the suction conduit 55 and flow down into the first chamber 20. Thus, depending on the desired maximum liquid level in the second chamber 40, the first end 55a may be positioned at a different elevation.

In some exemplary embodiments, the second end 55b may extend into the first chamber 20, and the elevational position of the second end 55b in the first chamber 20 may correspond to the desired maximum liquid level in the first chamber 20. For example, as the liquid level in the first chamber 20 rises above the elevational position of the second end 55b, the opening of the second end 55b may be closed by the rising liquid. Closing the opening may interrupt the suction communication between the first and second chambers 20, 40, thereby disabling the suction operation of the suction tube 78 and stopping the flow from the second chamber 40 into the first chamber 20.

Referring to FIGS. 3A and 3B, the system 10 may further comprise a support member 50 having a suitable valve mechanism for enabling selective draining of the second chamber 40. The support member 50 may include an annular body 52 configured to receive the outer wall 48a of the base member 48. In some exemplary embodiments, the annular body 52 and the base member 48 may be rotatable relative to each other. To guide the rotational movement, the outer tubular wall 48a may define a groove 47 or slot at least partially extending circumferentially around its outer surface, and the annular body 52 may include a projection 53 extending from its inner surface. In an alternative embodiment, the outer wall 48a may include the projection 53 extending from its outer surface, and the annular body 52 may define the corresponding groove 47 on its inner surface. To aid the rotational movement, at least one of the annular body 52 and the base member 48 may include a handle 49. As will be explained later, the handle 49 may also function as a position indicator for indicating whether the second chamber 40 is in a collecting mode or in a draining mode.

The support member 50 may also include a fitting sleeve 58 extending from the annular body 52 through a tapering shoulder portion 57. As best shown in FIG. 2, the fitting sleeve 58 may be sized and configured to fit into the second access port 21 of the first chamber 20. To facilitate its insertion into the second access port 21, at least the bottom end portion of the fitting sleeve 58 may be tapered. In some exemplary embodiments, when the fitting sleeve 58 is inserted into the second access port 21, the shoulder portion 57 may abut a mouth portion of the second access port 21 to more stably support the second chamber 40 on the first chamber 20. In addition, at least one of the second access port 21 and the fitting sleeve 58 may comprise a suitable sealing member (e.g., rubber neck) to seal the connection in a leak-tight manner.

As shown in FIGS. 3A and 3B, the support member 50 may include a plate member 51 defining a central hole, through which the suction conduit 55 may pass, and a valve opening 56 configured to selectively align with the opening 46 of the base member 48 to selectively open and close the flow passage between the first and second chambers 20, 40. For example, as shown in FIG. 3B, to open the flow passage, the base member 48 and/or the support member 50 may be rotated relative to one another to align the opening 46 of the transverse wall 48b with the opening 56 of the plate member 51. Where the base member 48 is integrally formed with the main body 45, the main body 45 may be rotated to cause the rotational movement of the base member 48. The aligned openings 46, 56 may allow the liquid collected in the second chamber 40 to be drained into the first chamber 20. In certain exemplary embodiments, at least one of the openings 46, 56 may comprise a filter element to limit the size and amount of the solid particles that may be included in the liquid. To close the flow passage, the base member 48 and/or the support member 50 may be rotated relative to one another to misalign the openings 46, 56, as shown in FIG. 3A.

While FIGS. 3A and 3B show that the base member 48 is rotated 180° relative to the support member 50 to align and misalign the openings 46, 56, it should be understood that, so long as the openings 46, 56 can be aligned and misaligned, the base member 48 and/or the support member 50 may be rotated less than 180°. It should also be understood that the transverse wall 48b and/or the plate member 51 may include a plurality of openings 46, 56. To prevent any leakage, including during rotational movements, the base member 48 and the support member 50 may include suitable sealing members 43, 54 (e.g., O-rings disposed in circumferential grooves around the openings 46, 56). As mentioned above, the handle 49 or any other suitable indication member known in the art may be used to indicate whether the openings 46, 56 are aligned or not (i.e., whether the system is in the liquid collection mode or in the liquid draining mode).

In an alternative embodiment, at least a portion of the support member 50 may be replaced with a simple actuatable valve (e.g., gate valve, rotary valve, pipe valve, or flap valve) that may selectively open and close the opening 46 of the base member 48. For example, instead of the plate member 51 of the support member 50, the base member 48 may include an actuatable gate valve that can selectively open and close the opening 46 of the base member 48. This embodiment may permit switching from a liquid collection mode to a liquid draining mode by simply actuating the valve without necessarily rotating the base member 48 or the support member 50. Since no rotational movement is required between the base member 48 and the support member 50, the base member 48 and the support member 50 may be integrally formed as a single piece. Alternatively, the support member 50 may be completely removed and, instead, the outer wall 48a may be modified to directly engage the first access port 21 of the first chamber 20.

Figure 4:
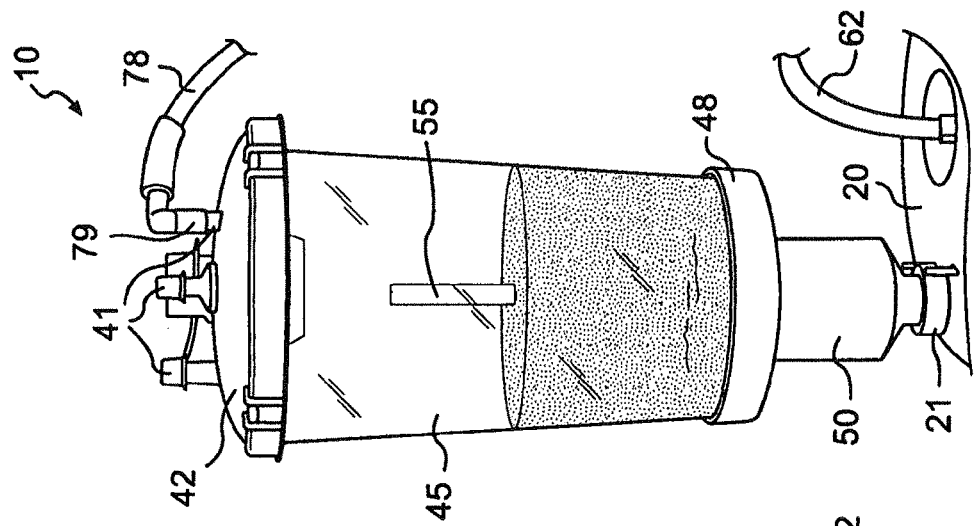
FIG. 4 is a perspective view of the second chamber of FIG. 1, illustrating the liquid collection process.
Figure 5:
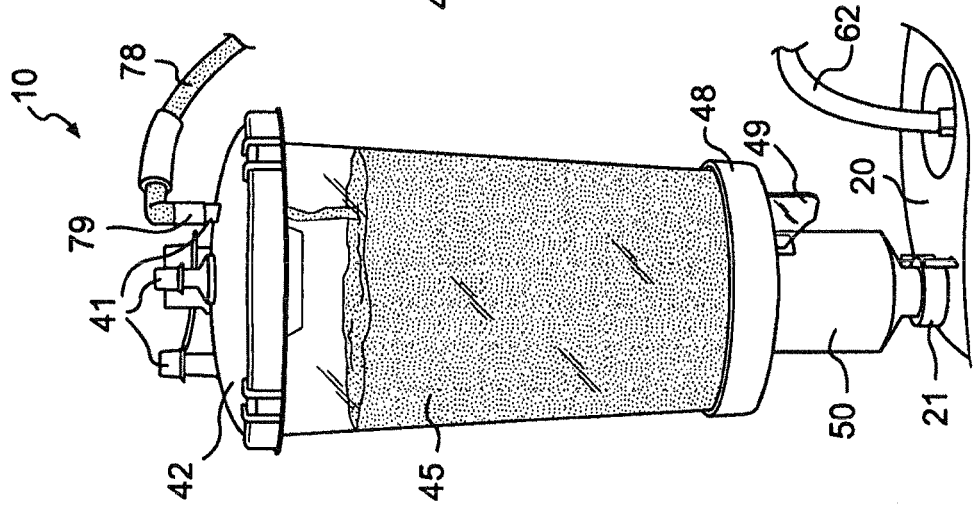
FIG. 5 is a perspective view of the second chamber of FIG. 1, illustrating the liquid collection process when the second chamber is full.
Figure 6:
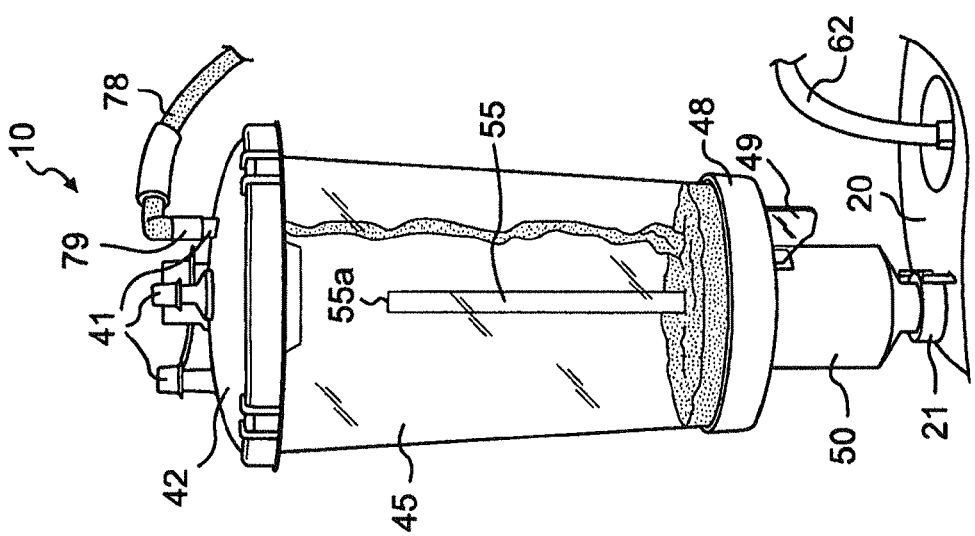
FIG. 6 is a perspective view of the second chamber of FIG. 1, illustrating the liquid draining process.

With reference to FIGS. 4-6, operational characteristics of the liquid collection system 10, according to various exemplary embodiments, will be explained. To set up the system 10, the suction source 60 may be connected to the first chamber 20 via the suction line 62, and the second chamber 40 may be attached to the first chamber 20. As discussed above, inserting the fitting member 58 of the support member 50 into the second access port 21 of the first chamber 20 may automatically establish both the suction connection and the fluid connection between the first and second chambers 20, 40, thereby eliminating the otherwise cumbersome, labor-intensive connection processes between the first and second chambers 20, 40. Once the second chamber 40 is properly positioned, the lid 42 may be placed on the main body 45 of the second chamber 40, and the suction tube 78 may be connected to the connecting port 41. If the medical procedure involves an additional medical device that requires suction, the device may be connected to the additional connecting port 41.

Once the setup is complete, the suction source 60 may be turned on to start the liquid collection process, as shown in FIG. 4. At this stage, as mentioned above, the opening 46 of the base member 48 may be closed by the plate member 51. While the liquid is being collected in the second chamber 40, the suction conduit 55 may continue to feed the suction power to the second chamber 40 from the first chamber 20.

Certain medical procedures may require collection of a large volume of liquid, which may exceed the maximum volume of the second chamber 40. In those cases, the suction conduit 55 may function as an overflow passage to continuously handle the liquid collection without interruption. For example, when the liquid level in the second chamber 40 rises above the first end 55a of the suction conduit 55, as shown in FIG. 5, the liquid above the first end 55a may flow down into the suction conduit 55 (via a combination of gravity and suction force from the first chamber 20) and into the first chamber 20.

After completion of the medical procedure, the liquid collected in the second chamber 40 may be drained into the first chamber 20, as shown in FIG. 6. To drain the liquid, the base member 48 may be rotated to align its opening 46 with the opening 56 of the support member 50. In some exemplary embodiments, the liquid collected in the second chamber 40 may be treated prior to transfer to the first chamber 20. The treatment may include, but not be limited to, sanitization, sterilization, or filtration. The sanitization and sterilization may include adding suitable chemicals (e.g., chlorine, hydrogen peroxide, etc.) or heating the liquid to a high temperature. In an exemplary embodiment, the second chamber 40 may include a filtration element, such as, for example, an aseptic filter or gross filter, to limit the size and amount of solids that may flow into the first chamber 20.

Once the liquid in the second chamber 40 is fully drained into the first chamber 20, the second chamber 40 may be removed from the system 10 and, for a subsequent medical procedure, a new second chamber 40 may be installed. The removed second chamber 40 may be simply placed in a waste storage container (e.g., red bag), along with its peripherals (e.g., tubes and connectors, etc.), for disposal. If desired, the used second chamber 40 may be cleaned and/or disinfected for reuse.

Figure 7:
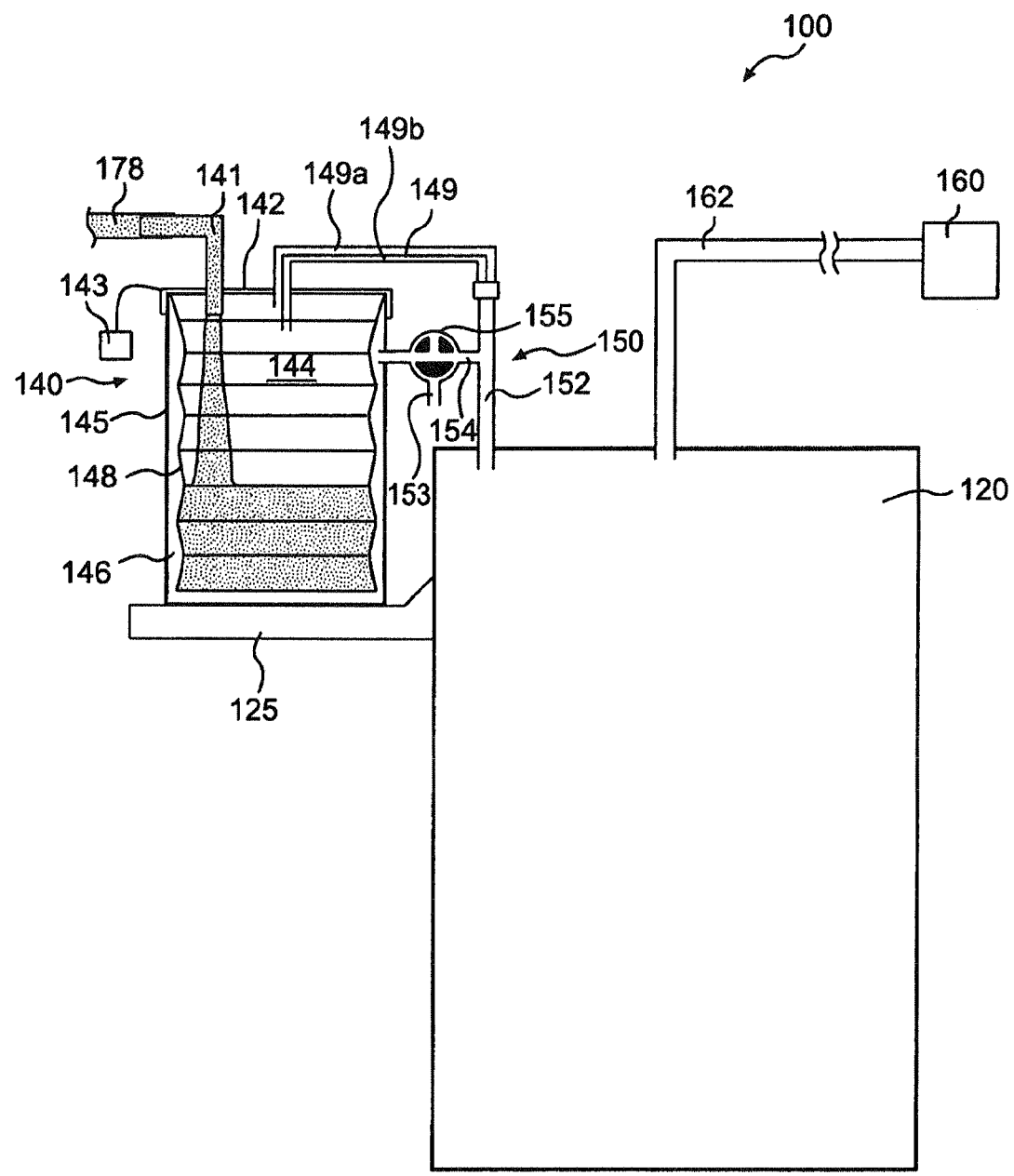
FIG. 7 is a schematic view of a liquid collection system, according to another exemplary embodiment of the invention, illustrating a liquid collection process.
Figure 8:
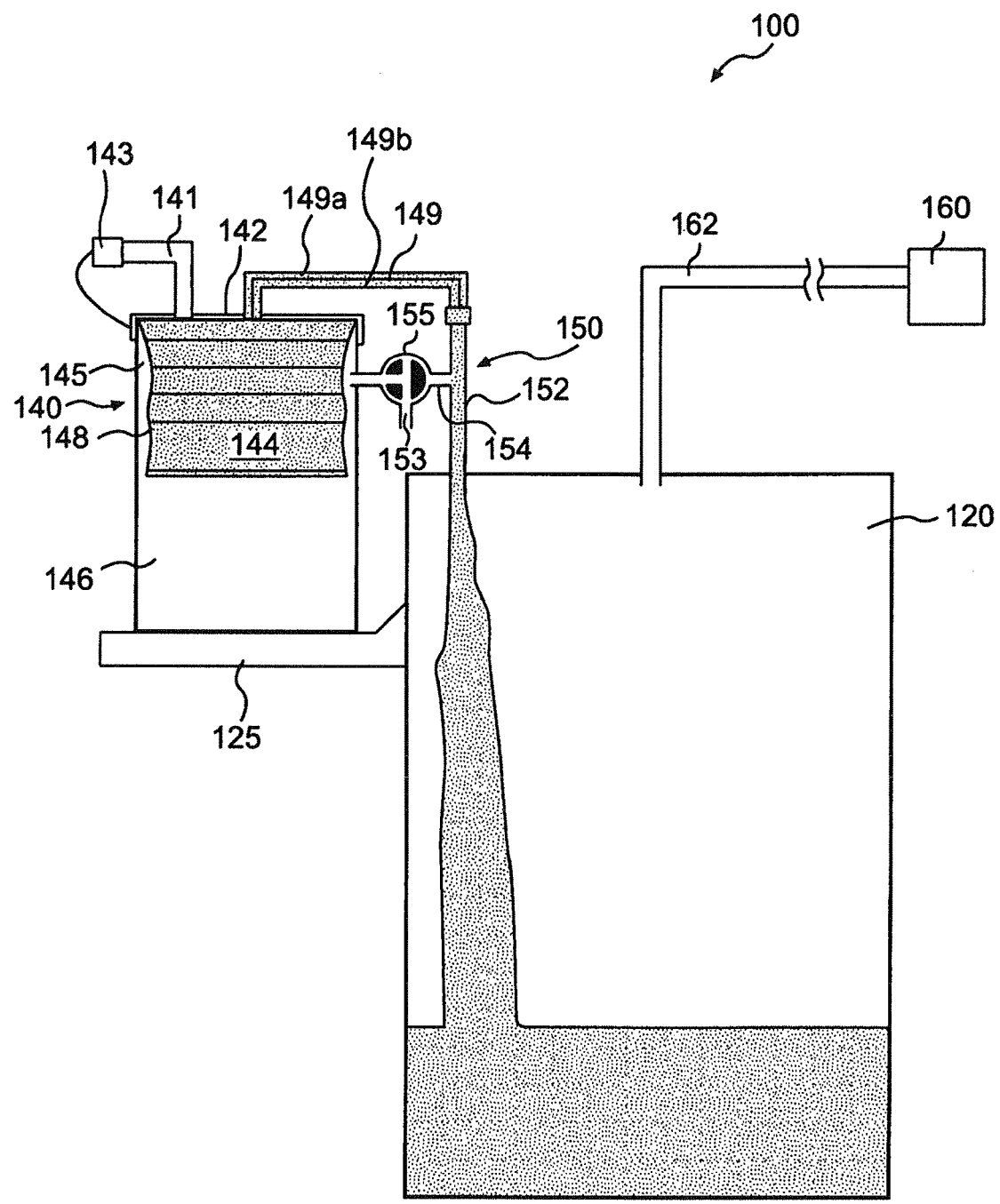
FIG. 8 is a schematic view of the liquid collection system of FIG. 7, illustrating a liquid draining process.

FIGS. 7 and 8 show a multi-chamber liquid collection system 100, according another exemplary embodiment consistent with the invention. Similar to the embodiment shown in FIGS. 1-6, the system 100 may comprise a first chamber 120 and a second chamber 140, where the volume of the first chamber 120 is substantially greater than the volume of the second chamber 140. The embodiment shown in FIGS. 7 and 8 may differ from the embodiments shown in FIGS. 1-6 in that, as will be described in detail herein, this embodiment may utilize a flexible liner 148 positioned inside the second chamber 140. The flexible liner 148 may prevent direct contact between the second chamber 140 and the liquid collected inside the second chamber 140. This may eliminate the need for replacing the entire second chamber 140 and, thereby, reduce the overall volume of waste generated in the medical facility. For example, after the medical procedure is completed, only the flexible liner 148 and its peripherals (e.g., lid, tubes, and/or connectors) may need to be disposed and replaced.

As shown in FIG. 7, the first chamber 120 may be connected to a suction source 160 via a suitable suction line 162 to generate a negative pressure (e.g., vacuum condition) inside the first chamber 120. The first chamber 120 may then communicate with the second chamber 140 via a suitable suction conduit 150 to generate a negative pressure inside the second chamber 140. This negative pressure inside the second chamber 140 may be used to drain liquid or secretions from a patient during a medical procedure. In some exemplary embodiments, the first chamber 120 may include a holding platform 125, on which the second chamber 140 may be placed. Unless otherwise noted, the configuration and operational characteristics of the first chamber 120 are substantially similar to those of the embodiment shown in FIGS. 1-6 and, therefore, a detailed description thereof will be omitted herein.

The second chamber 140 may comprise a main body 145, a lid 142, and a flexible liner 148 disposed inside the main body 145. The lid 142 may close the top opening of the main body 145 and create a liquid-tight, vacuum-tight seal therebetween. The lid 142 may include a first connecting port 141 and a second connecting port 149, both in communication with an interior of the second chamber 140. The first connecting port 141 may be used to connect to a suction tube 178 via a suitable connector, and the second connecting port 149 may be used to connect to the first chamber 120.

The second connecting port 149 may define two separate passages: a suction passage 149a and a liquid passage 149b. The liquid passage 149b may extend further down into the interior space 144 than the suction passage 149a and the first connecting port 141 so as enable continuous operation of the collection system 100 without interruption. As will be described in detail herein, both the suction and liquid passages 149a, 149b may function as a suction passage until the liquid level inside the interior space 144 reaches the opening of the liquid passage 149b. The lid 142 may also include a closure cap 143 configured to close the first connecting port 141. In various exemplary embodiments, the lid 142 may include additional connecting ports 141 with additional closure caps 143.

As shown in FIG. 7, the flexible liner 148 and the lid 142 may define the substantially sealed interior space 144 with the first and second connecting ports 141, 149 being the only connections to outside the interior space 144. In some exemplary embodiments, the flexible liner 148 may be integrally formed with, or configured to attach to, the inner surface of the lid 142. Thus, when the first and second connecting ports 141, 149 are closed, the interior space 144 may be substantially fully enclosed. The flexible liner 148 may be made of a sufficiently durable, yet collapsible material, so that, upon applying a negative pressure inside the interior space 144, the liner 148 can collapse into a smaller volume. In an exemplary embodiment, the flexible liner 148 may be configured to collapse in a predetermined manner. For example, as shown in FIG. 7, the flexible liner 148 may have a bellow-like configuration.

Like the second chamber 40 of the embodiment shown in, for example, FIGS. 1 and 2, the second chamber 140 may be at least partially transparent to enable the medical personnel to examine the content and amount of liquid collected in the second chamber 140. The main body 145 may also include volume graduations to more accurately measure the liquid amount collected in the second chamber 140.

As mentioned above, the first chamber 120 may communicate with the second chamber 140 via the suitable suction conduit 150. The suction conduit 150 may comprise a main line 152 and a branch line 154. The connection between the main line 152 and the branch line 154 may be configured such that, during a draining operation, fluid flowing through the main line 152 does not flow into the branch line 154. For example, the main line 152 or the branch line 154 may include a one-way valve (e.g., a flapper valve or a diaphragm) that allows fluid flow in only one direction.

Figure 7A:
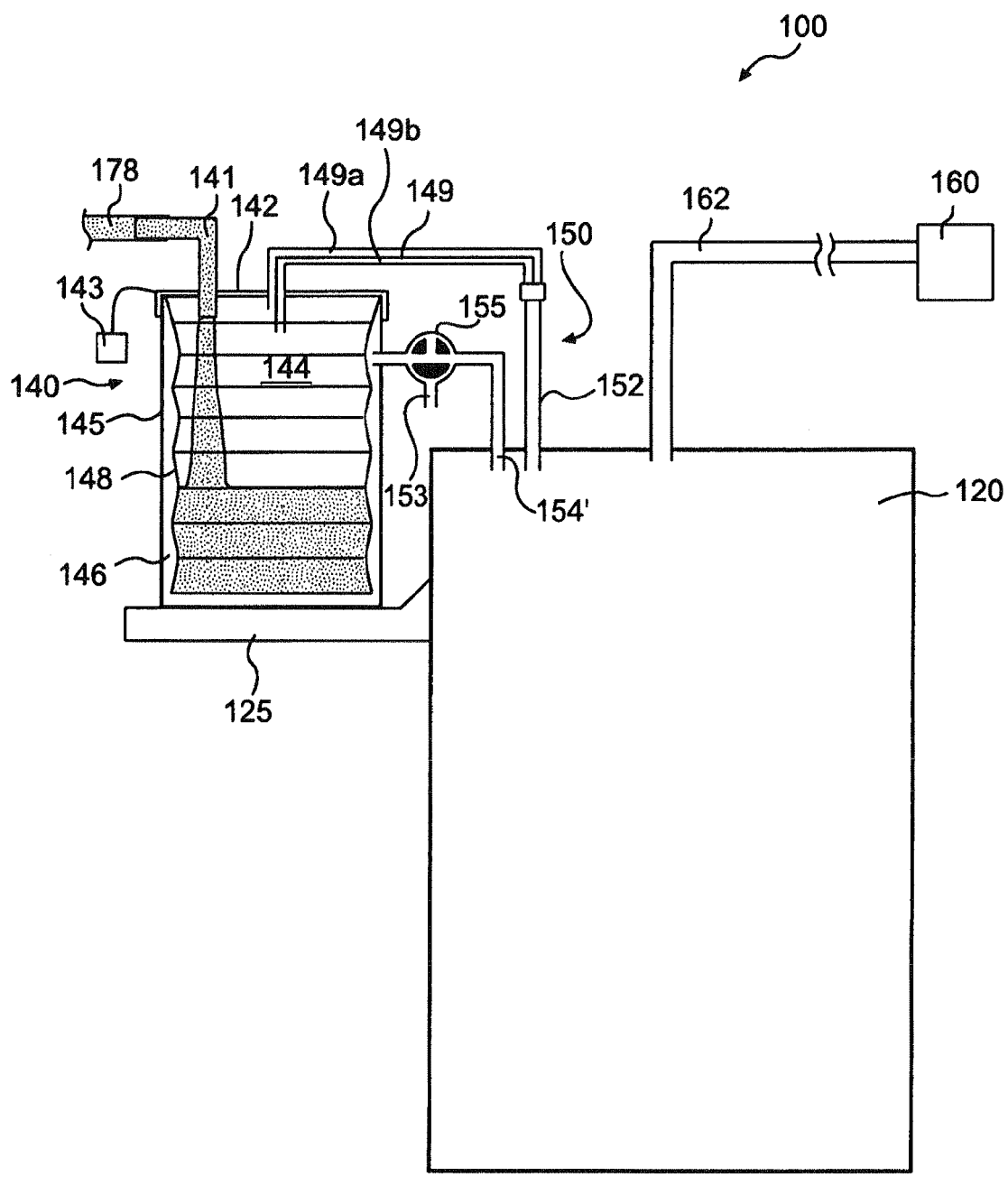
FIG. 7A is a schematic view of a liquid collection system, according to another exemplary embodiment of the invention.

In some exemplary embodiments, instead of having the branch line 154 branched from the main line 152, the system 100 may include a separate line 154' that independently connects to the first chamber 120, as shown in FIG. 7A.

The main line 152 may connect to the second connecting port 149 to communicate with the interior space 144 inside the flexible liner 148, and the branch line 154 may communicate with an exterior space 146 defined between the outer surface of the flexible liner 148 and the inner surface of the second chamber 140. The branch line 154 may include a suitable valve 155 to selectively open and close the branch line 154. As will be explained in more detail herein, when the valve 155 is open, the pressures inside the interior space 144 and the exterior space 146 may be substantially the same (e.g., substantially at vacuum condition). Conversely, when the valve 155 is closed, the suction force from the first chamber 120 may apply only to the interior space 144 and, therefore, the pressure inside the interior space 144 may be substantially less than the pressure inside the exterior space 146, which may cause the flexible liner 146 to collapse, as shown in FIG. 8.

In some exemplary embodiments, the valve 155 may comprise a three-way valve that, when the valve 155 closes the branch line 154, can establish fluid communication between the exterior space 146 and atmosphere 153. During the draining operation, this arrangement may allow the pressure inside the exterior space 146 to reach atmospheric pressure, so as not to interfere with the collapse of the liner 148.

With reference to FIGS. 7-10, a method of using the liquid collection system 100, according to various aspects of the invention, will be explained in detail. Prior to performing a medical procedure, the lid 142, including the first and second connecting ports 141, 149 and the flexible liner 148, may be placed on the main body 145 of the second chamber 140. The first connecting port 141 may then be connected to the suction tube 178, and the main line 152 and the branch line 154 of the suction conduit 150 may connect to the second connecting port 149 and the exterior space 146, respectively. Where the medical procedure involves an additional medical device that requires suction, the device may be connected to an additional connecting port (not shown) of the lid 142. In some exemplary embodiments, the suction conduit 150 may be integrally formed with at least one of the first and second chambers 120, 140, which may reduce the number of connections to be made by the medical personnel.

After the initial set up is completed, the suction source 160 may be turned on to start the liquid collection process, as shown in FIG. 7. At this stage, the valve 155 in the branch line 154 of the suction conduit 150 may be opened, and the suction force from the first chamber 120 may be equally applied to the interior space 144 and the exterior space 146 via the main line 152 and the branch line 154. Consequently, the opened valve 155 does not affect the flexible liner 148 or the volume of the interior space 144. Nor does it affect the suction capability of the suction tube 178. Once the liquid enters the interior space 144, the liquid may flow down into the interior space 144 via gravity.

Where the liquid level in the interior space 144 rises and reaches the opening of the liquid passage 149b, the liquid may be suctioned out of the interior space 144 into the first chamber 120 through the main line 152. At this stage, although the liquid passage 149b may be filled with liquid (i.e., liquid drawn from the second chamber), the suction passage 149a having an end positioned at an higher elevation than the end of the liquid passage 149b may remain open and continue to supply the suction force to the interior space 144. Thus, the liquid passage 149b may function as an overflow mechanism. In an alternative embodiment, the second connecting port 149 may have two separate conduits: one for the suction passage 149a and the other for the liquid passage 149b.

After the medical procedure is completed, the liquid collected in the interior space 144 may be drained into the first chamber 120. To drain the liquid, the suction tube 178 may be disconnected from the first connecting port 141, and the cap 143 may be used to close the first connecting port 141. The valve 155 may also be closed to shut off the supply of suction force to the exterior space 146 and allow fluid communication between the exterior space 146 and atmosphere. Disconnecting the suction tube 178 and/or closing the valve 155 may be performed while the suction source 160 is turned off. These steps, however, may be performed while the suction source 160 is still turned on.

Once the valve 155 is closed and the first connecting port 141 is closed, the interior space 144 may communicate only with the main line 152 of the suction conduit 150. With the suction source 160 turned on, the negative pressure inside the first chamber 120 may cause the flexible liner 146 to collapse, reducing the volume of the interior space 144, as shown in FIG. 8. The reduction in the volume may cause the liquid to be lifted and drained into the first chamber 120 through the second connecting port 149.

Figure 9:
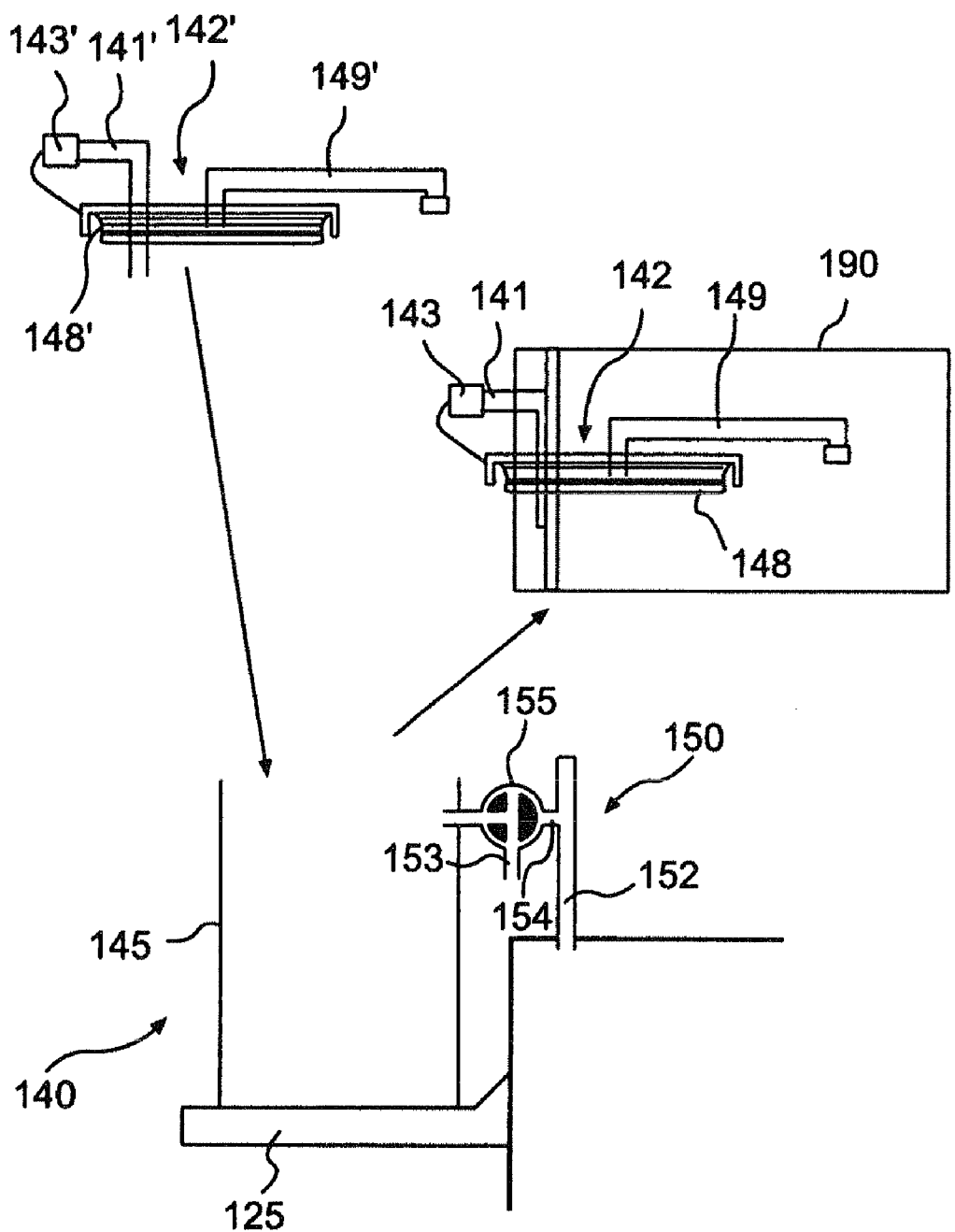
FIGS. 9 and 10 are schematic illustrations of a disposal and setup process for a new medical procedure.
Figure 10:
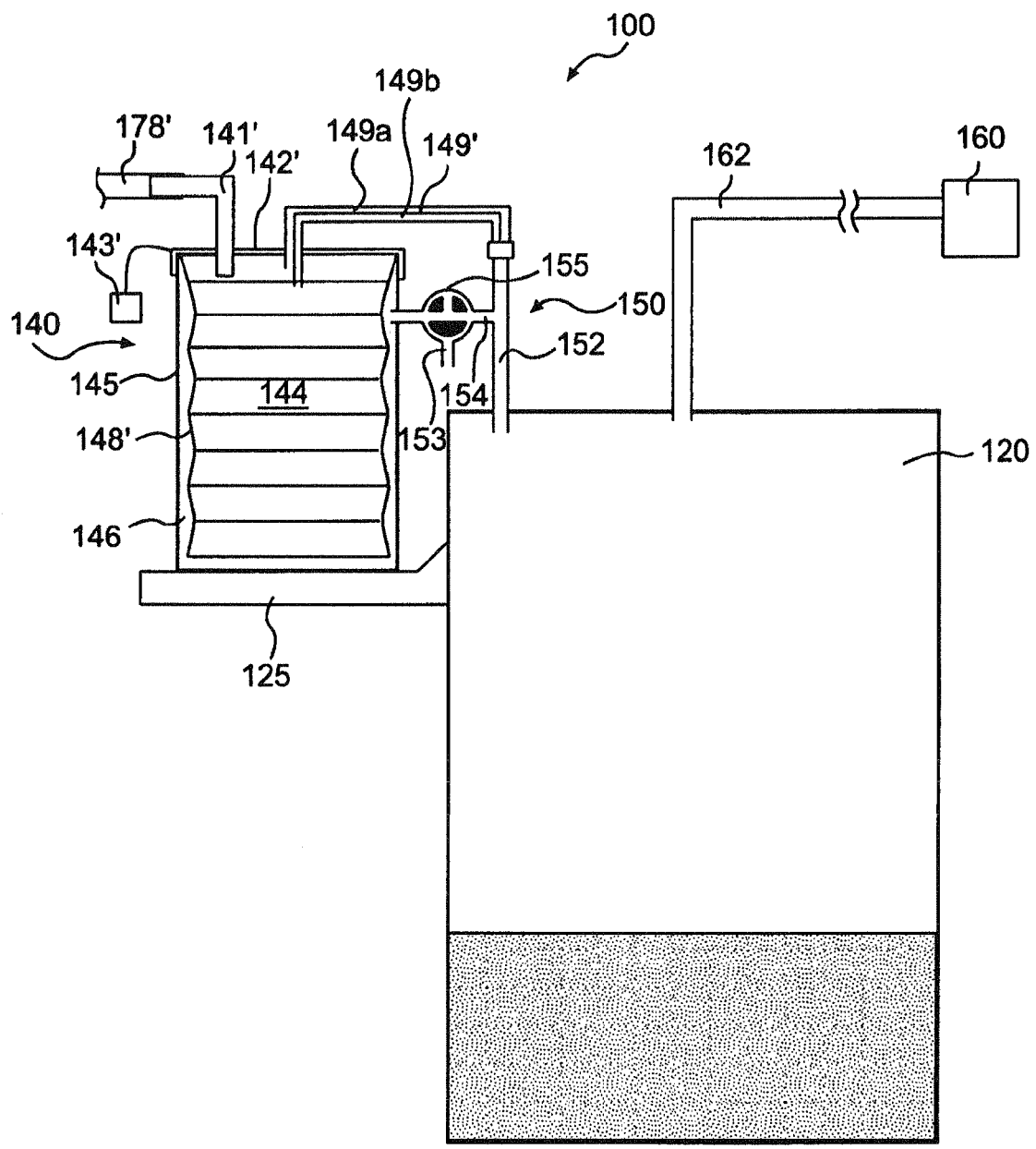

As shown in FIG. 9, after the liquid in the second chamber 140 is completely drained, the suction source 160 may be turned off. The second connecting port 149 may then be disconnected from the suction conduit 150, and the lid 142 may be removed from the main body 145 along with its peripherals (e.g., the first and second connecting ports 141, 149, the closure cap 143, and the flexible liner 148). The removed lid 142 and its peripherals 141, 143, 148, 149 may be placed in a waste storage container 190 (e.g., red bag) for disposal. Thereafter, a new package containing a new lid 142' (containing new connecting ports 141', 149' and cap 143') and a new flexible liner 148' may be placed onto the main body 145. After various tubes and ports are properly connected, the system 100 may be ready for a new medical procedure, as shown in FIG. 10.

In some exemplary embodiments, the liquid collected inside the second chamber 140 may be treated (e.g., sanitization, sterilization, or filtration) before it is drained to the first chamber 120. For example, the liquid may be sanitized and/or sterilized by adding appropriate chemical agents, such as chlorine or hydrogen peroxide, or by heating at a high temperature. Alternatively or additionally, the liquid may be filtered. Gross filtration of the liquid before being transferred to the first chamber 120 may reduce the size and amount of solids that may have to be eventually disposed of from the first chamber 120.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical waste fluid collection system for collecting medical waste during a medical procedure, comprising:
 a first fluid chamber in fluid communication with a suction source;
 a second fluid chamber defining an internal space and located externally to the first fluid chamber, the second fluid chamber including a connector port for connecting to a suction tube through which medical waste fluid is collected in the internal space of second fluid chamber;

a drainage port configured to selectively drain the medical waste fluid collected in the internal space of the second fluid chamber into the first fluid chamber; and a transport unit comprising a flat platform and wheels, wherein the first fluid chamber is secured to the flat platform, wherein the suction source is integrally formed with the transport unit, and wherein at least one of the first fluid chamber and the second fluid chamber comprises a transparent material having volume graduations thereon for providing accurate measurement of the fluid collected in the respective fluid chamber.

2. The medical waste fluid collection system of claim 1, further comprising:

a volume control mechanism located at least partially within the internal space of the second fluid chamber and extending through an outlet port of the second fluid chamber, wherein the drainage port is configured to selectively drain the medical waste fluid collected in the internal space second fluid chamber into the first fluid chamber when the fluid collected in the internal space of the second chamber has exceeded a demarked fluid level indicated via the volume control mechanism.

3. The medical waste fluid collection system of claim 2, wherein the volume control mechanism is an overflow device.

4. The medical waste fluid collection system of claim 2, wherein the volume control mechanism is a conduit.

5. The medical waste fluid collection system of claim 2, wherein the volume control mechanism comprises a conduit including a first end located in the first fluid chamber and a second end extending through and encompassed by the drainage port.

6. The medical waste fluid collection system of claim 2, wherein the volume control mechanism is adjacent the drainage port.

7. The medical waste fluid collection system of claim 1, wherein the second fluid chamber has a smaller volume capacity than the first fluid chamber.

8. The medical waste fluid collection system of claim 1, wherein first fluid chamber comprises a cap, the cap including a first access point for communicating with the suction source and a second access port for communicating with the second fluid chamber.

9. The medical waste fluid collection system of claim 1, wherein the second fluid chamber is located in an elevated position relative to the first fluid chamber.

10. The medical waste fluid collection system of claim 1, further comprising:

a conduit configured to communicate at least among an opening located in a vapor space of the second fluid chamber and an opening located in a vapor space of the first fluid chamber.

11. The medical waste fluid collection system of claim 1, wherein the second fluid chamber comprises an inlet port connected to an external tube.

12. The medical waste fluid collection system of claim 1, wherein the second fluid chamber comprises a lid, the lid including one or more ports for connection to external equipment.

* * * * *